US005635487A

United States Patent [19]

Wolff et al.

[11] Patent Number: 5,635,487

[45] Date of Patent: Jun. 3, 1997

[54] AMPHIPATHIC, MICELLAR DELIVERY SYSTEMS FOR BIOLOGICALLY ACTIVE POLYIONS

[76] Inventors: Jon A. Wolff, 1122 University Bay Dr.;
Vladimir Budker, 204 N. Segoe Rd. #513, both of Madison, Wis. 53705;
Vladimir Gurevich, 2113 E. Johnson St., Madison, Wis. 53704

[21] Appl. No.: 368,150

[22] Filed: Dec. 29, 1994

[51] Int. Cl.$^6$ .......................... A61K 48/00; A61K 31/66; A61K 31/415

[52] U.S. Cl. .......................... 514/44; 424/490; 424/498; 424/502; 935/54; 548/341.5; 514/400

[58] Field of Search .......................... 424/490, 498, 424/502; 514/44, 400; 935/54; 548/341.5

[56] References Cited

U.S. PATENT DOCUMENTS 5,151,264  9/1992  Samain et al. .......................... 424/1.21

OTHER PUBLICATIONS

Behr J.P., Demeneix B., Loeffler J.P., Perez-Mutul J. Efficient Gene Transfer into Mammalian . . . P.N.A.S. 86:6982-6986 Sep. 1989.

Primary Examiner—Jacqueline M. Stone
Assistant Examiner—Patrick Twomey
Attorney, Agent, or Firm—Dressler, Rockey, Milnamow & Katz, Ltd.

[57] ABSTRACT

The present invention provides a composition comprising a population of micelles wherein each micelle comprises at least one amphipathic compound layer that surrounds a non-aqueous core that contains a polyion. Also provided are a method of preparing such a composition and the uses of such compositions for delivering biologically active polyions to cells.

5 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGCGTTCTTC CATTTTACC                    19

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:2:

GGTAAAATGG AAGACGCC                           18

AMPHIPATHIC, MICELLAR DELIVERY SYSTEMS FOR BIOLOGICALLY ACTIVE POLYIONS

TECHNICAL FIELD OF THE INVENTION

The technical field of the present invention is micellar compositions comprising amphipathic compounds and biologically active polyions and the use of such compositions to deliver polyions to cells.

BACKGROUND OF THE INVENTION

The efficient delivery of biologically active compounds to the intracellular space of cells has been accomplished by the use of a wide variety of vesicles. One particular type of vesicle, liposomes, is one of the most developed types of vesicles for drug delivery. Liposomes are microscopic vesicles that comprise amphipathic molecules that contain both hydrophobic and hydrophilic regions. Liposome drug carriers have been under development since the 1970's. Liposomes are formed from one to several different amphipathic molecules. Several methods have also been developed to complex biologically active compounds with liposomes.

Polynucleotides have been typically delivered to mammalian cells complexed with liposomes containing amphipathic compounds. The liposomes consist of a bilayer surrounding an aqueous core. The present invention provides that new methods can be used to prepare novel complexes of biologically active polyions and amphipathic compounds. These novel micellar compositions comprise a population of monolayer or bilayer micelles containing the polyions within an internal, non-aqueous core of the micelle.

BRIEF SUMMARY OF THE INVENTION

In one aspect the present invention provides a composition comprising a population of micelles wherein each micelle comprises at least one amphipathic compound layer that surrounds a non-aqueous core that contains a biologically active polyion. In one embodiment, the polyion is a polyanion and the amphipathic compound is cationic. A preferred polyanion for use in a composition is a polynucleotide such as an RNA or a DNA molecule.

The population of micelles can comprise mixed micelles of different composition, namely anisotrophic micelles. Still further, the micelles can be monolayer or bilayer micelles. Where the micelles are bilayer micelles, those micelles comprise an inner and an outer layer, wherein the inner layer comprises one or more amphipathic compound and the outer layer comprises one or more amphipathic compound. The amphipathic compounds that comprise the inner layer can be different from the amphipathic compounds that comprise the outer layer.

Where the micelle is a monolayer micelle, the hydrophilic component of the major amphipathic compound has a charge opposite to that of the polyion suspended in the non-aqueous core (e.g., where the polyion is a polyanion, the amphipathic compound is cationic). Where the micelle is a bilayer micelle, the major component in the inner layer of the micelle has a charge opposite to that of the polyion suspended in the non-aqueous core. In a preferred embodiment, where the polyion is yanionic polynucleotide, the amphipathic compound is Compound 20.

In another aspect, the present invention provides a process of preparing a population of micelles comprising mixing an amphipathic compound with a biologically active polyion in an aqueous solution containing at least five volumes percent of a water-soluble organic solvent to form the micelles. Exemplary and preferred water-soluble organic solvents are ethanol, isopropanol, methanol, and acetonitrile.

A process of the present invention can be used to prepare bilayer micelles by further mixing the formed monolayer micelles with an additional amphipathic compound in organic solvents to form an admixture and then decreasing the concentration of the water-soluble organic solvent in the admixture. Moreover, two anisotropic layers can be formed by adding amphipathic compounds with a different affinity to the polyion at the same time without preformed monolayer micelles. For example, if a mixture of a positively charged lipid and a neutral lipid were added to DNA, the lipids would naturally segregate so that the first layer would contain the positively charged lipid and the second layer would contain the neutral layer after removal of the organic solvent.

In still yet another aspect, the present invention provides a process of delivering a biologically active polyion to a cell comprising exposing the cell to an effective amount of a composition comprising a population of micelles wherein each micelle comprises at least one amphipathic compound layer that surrounds a non-aqueous core that contains the polyion. In a preferred embodiment, the polyion is a polynucleotide such as RNA, DNA or a protein molecule. In one embodiment, a process of delivering a polynucleotide to a cell can be used to express a gene product in that cell. In accordance with that embodiment, the polynucleotide is an encoding DNA molecule or mRNA molecule. In another embodiment, a process of delivering a polynucleotide to a cell can be used to inhibit gene product expression in that cell. In accordance with that process, the polynucleotide is an antisense molecule directed against a DNA or RNA encoding that product.

A process of delivering a polyion to a cell can be used where that cell is located in vitro (e.g., in culture) or in vivo (in a living organism such as a mammal). Where the cell is located in vitro, the cell is exposed to the composition by adding the composition to the medium in which the cell is cultured. Where the cell is located in vivo, the composition is administered to the living organism. Exemplary and preferred routes of administration are direct injection into tissue or parenteral administration via the circulation (e.g., intavenous or intraarterial) or by topical administration to the skin.

DETAILED DESCRIPTION OF THE INVENTION

I. The Invention

Polynucleotides have been typically delivered to mammalian cells complexed with liposomes containing amphipathic compounds. The liposomes consist of a bilayer surrounding an aqueous core. The present invention provides that new methods can be used to prepare novel complexes of biologically active polyions and amphipathic compounds. These novel micellar compositions comprise a population of monolayer or bilayer micelles containing the polyions within an internal, non-aqueous core of the micelle.

A new process of forming such micellar compositions comprises mixing the amphipathic compounds and polyion within solutions containing a high concentration of a water-soluble organic solvent such as ethanol, methanol, isopropanol, or acetonitrile. The amount of the amphipathic compound is sufficient to form a monolayer surrounding the polyion. Additional amphipathic compounds can be added to provide material for bilayer micelles. The second, or outer, layer can have a different composition than the first, or inner, layer. The first and second steps can be combined into one step. The concentration of the organic solvent is decreased to levels that are appropriate for the applications. The second layer forms during this step. This decrease in the concentration of the organic solvent can be accomplished by a variety of standard methods well known in the art such as dilution into water or dialysis.

The micelles can be anisotropic in which the inner layer in contact with the polyion is of one type of composition and the outer layer has another composition. Composition means different types of lipids in different proportions.

II. Micellar Compositions

In one aspect, the present invention provides a composition comprising a population of micelles, wherein each micelle comprises at least one amphipathic compound that surround a non-aqueous core containing a biologically active polyion. As is well known in the art, the phrase "amphipathic compound" means a compound having both a hydrophobic and a hydrophilic component. Amphipathic compounds are well known in the art. By way of example, negatively charged anionic ampipathic compounds, negatively charged, pH-sensitive amphipathic Compounds and cationic compounds have been previously described. By way of example, negatively-charged, pH-sensitive liposomes have been used to deliver DNA in a functional and target-specific manner in vitro and in vivo. Negatively-charged, pH-sensitive liposomes have also been used to deliver proteins.

More efficient polynucleotide transfer in vitro has been accomplished with the use of positively-charged liposomes that contain cationic lipids. The cationic lipid, N-[1-(2,3-dioleyloxy)propyl]-N,N,N-trimethylammonium chloride (DOTMA) was the first cationic lipid used for DNA transfections. DOTMA was combined with dioleoylphosphatidylcholine (DOPE) to form liposomes that spontaneously complexed with polynucleotides (DNA and RNA) and enabled relatively efficient tranfections. These cationic liposomes are simply mixed with the polynucleotide and then applied to the cells in culture. Complete entrapment of the DNA or RNA molecules occurs because the positively-charged liposomes naturally complex with negatively-charged polynucleotides. DNA has been shown to induce fusion of cationic liposomes containing DOTMA/DOPE. The procedure with the cationic lipids is generally as or more efficient than the commonly-used procedure involving the co-precipitation of calcium phosphate and DNA.

A variety of cationic lipids have been made in which a diacylglycerol or cholesterol hydrophobic moiety is linked to a cationic headgroup by metabolically degradable ester bond. These have included 1,2-Bis(oleoyloxy)-3-(4'-trimethylammonio) propane (DOTAP), 1,2-dioleoyl-3-(4'-trimethylammonio) butanoyl-sn-glycerol (DOTB), 1,2-dioleoyl-3-succinyl-sn-glycerol choline ester (DOSC) and cholesteryl (4'-trimethylammonio)butanoate (ChoTB). Stearylamine, a cationic lipid has been used in liposomes but it had great cytotoxicity and had not been reported to mediate DNA transfer. Another detergent, cetyltrimethylammonium bromide (CTAB) when combined with DOPE was able to mediate DNA transfection. A series of cationic, non-pH sensitive lipids that included DORI (1,2-dioleoyl-3-dimethyl-hydroxyethyl ammonium bromide), DORIE (1,2-dioleyloxypropyl-3-dimethyl-hydroxyethyl ammonium bromide), and DMRIE (1,2-dimyristyloxypropyl-3-dimethyl-hydroxyethyl ammonium bromide) have been reported and studied. Other non-pH-sensitive, cationic lipids include: O,O'-didodecyl-N-[p-(2-trimethylammonioethyloxy)benzoyl]-N,N,N-trimethylammonium chloride, Lipospermine, DC-Chol (3β [N-(N', N"-dimethylaminoethane)carbonyl]cholesterol), lipopoly(L-lysine), cationic multilamellar liposomes containing N-(a-trimethylammonioacetyl)-didodecyl-D-glutamate chloride (TMAG), TransfectACE™ (1:2.5 (w:w) ratio of DDAB which is dimethyl dioctadecylammonium bromide and DOPE) (GIBCO BRL) and lipofectAMINE™ (3:1 (w:w) ratio of DOSPA which is 2,3-dioleyloxy-N-[20 ([20 ({2,5-bis[(3-aminopropyl)amino]-1-oxypentyl}amino) ethyl]-N,N-dimethyl-2,3-bis (9-octadecenyloxy)-1-propanaminium trifluoroacetate and DOPE) (GIBCO BRL).

In addition to the negatively charged, negatively charged pH-sensitive and cationic amphipathic compounds previously described, positively charged pH-sensitive amphipathic compounds can also be used in a composition of the present invent ion. A pH-sensitive, positively charged (cationic) amphipathic compound comprises:

(a) at least one hydrophobic moiety, each of which is selected from the group consisting of $C_6$–$C_{24}$ alkane, $C_6$–$C_{24}$ alkene, fatty acids, steroids, and steroid derivatives;

(b) at least one cationic, hydrophilic, pH-sensitive moiety comprising an amine, the positive charge of which pH-sensitive moiety increases with decreasing pH over the pH range of from about 8 to about 4.5; and (c) a spacer group linking the hydrophobic moiety and the cationic, pH-sensitive moiety, which spacer group is selected from the group consisting of $C_1$–$C_{12}$ alkane, $C_1$–$C_{12}$ alkene, ester, ether, glycerol, amide and heteroatoms.

The hydrophobic moiety can be an alkane, an alkene, a fatty acid or asteroid derivative. Preferably, the alkane and alkene comprise from about 6 to about 24 carbon atoms. In a like manner, a fatty acid preferably contains from 6 to 24 carbon atoms and, more preferably from about 12 to 20 carbon atoms. A fatty acid can be either saturated or unsaturated. In a preferred embodiment, the fatty acid is palmitic acid, oleic acid, stearic acid or myristic acid.

As used herein, the phrase "steroid derivative" means a sterol, a steroid, asteroid hormone, or an analog or derivative thereof. Preferred steroid derivatives are sterols, steroid hormones and analogs or derivatives thereof. Preferably, the sterol is cholesterol and the steroid hormone is dexamethasone.

The hydrophobic moiety and the hydophilic, cationic, pH-sensitive moiety are linked via a spacer group. The spacer group can be any linker known to those skilled in the art to enable one to join a hydrophobic moiety with the hydrophilic moiety. Preferred spacer groups include, but are not limited to $C_1$ to $C_{12}$ alkyl, $C_1$–$C_{12}$ alkenyl, ester, ether, glycerol, amide and heteroatoms. For example, the hydrophilic, cationic, pH-sensitive moiety can be linked to the same fatty acid though the use of a glycerol moiety, wherein the same fatty acids are linked to the glycerol moiety by an ester linkage. In another example, a cholesterol derivative is linked to a hydrophobic, cationic, pH-sensitive moiety through a heteroatom linkage, in particular a disulfide linkage or an amide linkage.

The hydrophobic moiety and hydrophilic, cationic, pH-sensitive moiety can also be linked via a spacer group or other linkage that is cleavable under physiological conditions (e.g., the intracellular environment). Exemplary such cleavable linkages are disulfide bridges or an enzyme-sensitive group. A detailed description of the preparation of exemplary and preferred such cationic, pH-sensitive amphipathic compounds is set forth hereinafter in Example 1.

The choice of a particular amphipathic compound in a composition of the present invention depends upon the nature of the polyion to be contained within the non-aqueous core of the micelle. The only limitation is that the charge of the hydrophilic portion of the amphipathic compound be opposite to the charge of the polyion in the non-aqueous core. By way of example, where the polyion is a polyanion (negatively charged), the amphipathic compound immediately surrounding the non-aqueous core should be cationic in nature. Thus, where the polyion is a polyanion, the amphipathic ion should be a cationic or pH-sensitive cationic amphipathic compound. Where the micelle is a bilayer micelle, the first amphipathic compound contained in the inner layer of that micelle should also be of opposite charge to that of the polyion contained in the non-aqueous core.

In a preferred embodiment, the amphipathic compound component of the micellar composition of the present invention further comprises a target recognition group. A target recognition group is a chemical group that recognizes and becomes associated with (e.g., binds to) a target cell. In this way, the composition can be used to deliver a biologically active polyion to a particular cell type. Exemplary target recognition groups are antibodies. A target recognition group can be attached to any component of the amphipathic compound using standard procedures well known to those skilled in the art.

Several advantages flow from the composition of the present invention. One of the advantages of the materials disclosed herein is that they permit efficient entrapment of polyions by an exceedingly convenient and practical protocol. Another advantage of the convenient and practical uses of the compositions as set forth hereinafter yields unique properties enabling entry of the entrapped polyions, such as DNA, into living cells. This property of the composition enables the expression of biological activities to extents not previously seen in these cells. The micellar compositions of this invention are pharmaceutically advantageous; these materials enable the better uptake of pharmaceutical materials by the cells. In addition, the compositions of the present invention provide a simple, convenient way to make and design anisotropic vesicles.

III. Process of Making Micellar Compositions

In another aspect, the present invention provides a process of preparing a population of micelles comprising an amphipathic compound surrounding a non-aqueous core containing a biologically active polyion. In accordance with that process, an amphipathic compound is mixed with a biologically active polyion in an aqueous solution containing at least 5 volumes % of a water-soluble organic solvent. Any water-soluble organic solvent can be used in a process of the present invention. Exemplary and preferred water-soluble organic solvents are ethanol, isopropanol, methanol and acetonitrile. In a preferred embodiment, the concentration of the water-soluble organic solvent is from about 5 to about 99.9 volumes %. Micelles formed as a result of such a process can be isolated using standard procedures well known in the art. Bilayer micelles (micelles containing an inner and an outer layer) can be prepared by mixing the formed micelles from the above process with a second amphipathic compound to form an admixture. The concentration of the water-soluble organic solvent in the admixture is then decreased to form the bilayer micelle. The concentration of the water-soluble organic solvent can be decreased using standard procedures well known in the art. By way of examples, the concentration can be decreased by diluting the solvent into water, via dialysis or by solvent evaporation. It should be noted, that some anisotropic micelles can be formed without decreasing the concentration of organic solvent. In addition, anisotropic micelles can be formed by simply mixing different amphipathic compounds as described above.

As set forth above, it is not necessary that the same amphipathic compounds be used to form both the inner and outer layer of bilayer micelles. Thus, where anisotropic micelles are to be formed, the amphipathic compounds used to form the outer most layer of the micelle can be different from the amphipathic compounds used to form the inner most layer of the micelle. The inner and outer layers of bilayer micelles can vary in charge as well as chemical composition. Each inner and outer layer can have more than one amphipathic compound. Thus, an inner layer of a bilayer micelle can comprise anionic amphipathic compounds while the outer layer can comprise cationic amphipathic compounds. The only limitation is that the charge of the hydrophilic portion of the amphipathic compounds comprising the inner most layer of the micelle is opposite to that of the charge of the polyanion disbursed in the non-aqueous core of the micelle.

IV. Methods of Use

A. A Process of Delivering a Biologically Active Polyion to a Cell

In another aspect, the present invention provides a process of delivering a biologically active polyion to a cell. In accordance with that process, a target cell (a cell to which the substance is to be delivered) is exposed to a micellar composition of the present invention. Preferred such compositions are the same as set forth above. A target cell can be located in vitro (cell culture), in situ or in vivo (in a living organism).

As used herein, the phrase "biologically active polyion" means any polyion having the ability to alter the function of a living cell, tissue or organism. A biologically active polyion can be a drug or other therapeutic agent. A biologically active polyion can also be a chemical that interacts with and alters the function of a cell. By way of example, a biologically active polyion can be a protein or peptide fragment thereof such as a receptor agonist or antagonist.

Preferably, a biologically active substance is a polyanion. A preferred polyanion is a polynucleotide. As used herein, a polynucleotide is meant to include both DNA and RNA sequences of varying length. A DNA polynucleotide can be a gene, transgene, oligonucleotide, antisense sequence, cDNA sequence and the like. In a similar manner, a RNA polynucleotide can be a complete mRNA molecule or a short antisense sequence. Also, the polyanion can be a mononucleotide or a mononucleotide derivative such as ATP.

Where the target cell is located in vitro, the micellar composition is typically added to the culture medium in which the cell is being cultured. Where the target cell is located in vivo, the composition is typically administered to the organism in such a way as to distribute the material to the cell. The composition can be infused into the cardiovascular system (e.g., intravenously, intraarterially), injected directly into tissue containing the target cell (e.g., intramuscularly) or administered via other parenteral routes well known to one skilled in the art such as topical delivery by administration to the skin.

As set forth above, a composition can be prepared so as to contain a target recognition group, which group serves to direct the biologically active polyion to particular cells with a high degree of efficiency.

B. Process of Transfecting a Cell with a Polynucleotide

Despite remarkable accomplishments in cloning genes relevant to many diseases and in developing a variety of new gene therapy methods in both animal and human models, there remains to be solved the challenging problem of efficiently transferring and stably expressing polynucleotides such as transgenes in appropriate tissues. Several new methods of gene transfer into postnatal somatic tissue are under development in many laboratories. They can be divided into two general approaches: those using direct transfer into cells in vivo and those using indirect methods involving the re-implantation of genetically-modified cells.

Indirect transplantation generally complicates a procedure in terms of risk, difficulty, efficacy, and cost. For example, bone marrow transplantation requires cytoablation, with accompanying mortality and morbidity. The transplantation of retrovirally infected hepatocytes requires a partial hepatectomy. Even if these experimental procedures eventually prove to be safe and effective, they may remain technically difficult to perform and costly, and therefore restricted in their availability. Direct gene therapy, on the other hand, is easier to perform and less risky, and therefore more widely applicable.

In another aspect, the present invention provides a process of transfecting a cell with a polynucleotide comprising exposing the cell to a micellar composition of the present invention that contains the polynucleotide. The cell can be located in vitro, in situ or in vivo. Means for exposing the cell are the same as set forth above. Any cell can be transfected with a process of the present invention. Preferably, the cell is a muscle cell and, more preferably a cardiac or skeletal muscle cell. Details of transfecting cells with a composition of the present invention are set forth hereinafter in the Examples.

Not only can a process of the present invention be used to transfect a cell but the transfection is shown to result in a marked increase in the expression of the transfected polynucleotide (See Examples, hereinafter). Thus, a composition of the present invention has use in a process of increasing polynucleotide expression in a cell.

The following Examples illustrate particular embodiments of the present invention and are not limiting of the claims and specification in any way.

EXAMPLE 1

Synthesis of pH-Sensitive, Cationic Amphipathic Compounds

Thin Layer Chromatography (TLC) Systems

System [1]-dichloromethane/methanol 9:1 TLC plates-Kieselgel 60F254 from EM Science System [2]-dichlormethane/methanol 8:2 TLC plates-Kieselgel 60F254 from EM Science System [3]-dichloromethane/methanol 6:4 TLC plates-Kieselgel 60F254 from EM Science System [4]-dichloromethane TLC plates-Kieselgel 60F254 from EM Science System [5]-heptane/ethylacetate 9:1 TLC plates-Baker-Flex cellulose System [6]-ethanol TLC plates-Baker-Flex cellulose System [7]-Acetonitrile/diethanolamine 9:1 TLC plates-Baker-Flex cellulose System[8]-45% methanol-45% tetrahydrofuran-10% acetic acid TLC plates-Whatman MKC18 reverse phase Compound 1

A. Structure $$CH_3(CH_2)_{14}-C(=O)-O-CH_2$$
$$CH_3(CH_2)_{14}-C(=O)-O-CH$$
$$CH_2-C=N-C=N(CH_3)$$

B. Synthesis 136 mg (0.2 mmol) of 1,2-dipalmitoyl-3-iodo-rac-3-deoxyglycerol was dissolved in 2 μl of dioxane and mixed with 24 μl (0.3 mmol) of 1-methylimidazole. The reaction mixture was then stirred for 16 hours at 70° C. Dioxane was evaporated and the residue was dissolved in chloroform and mixed with an equal volume of double-distilled water. After centrifugation and separation, the water layer was discarded. This extraction with water was repeated twice more. The chloroform layer was mixed with 3 volumes of acetonitrile and two thirds of the mixture volume was slowly evaporated under vacuum. Title Compound 1 was collected as a filtrate and dried under vacuum overnight. Yield was 128 mg (84% of the theoretical yield) of white crystals with:

Melting point 86°±1° C.

$R_f$=0.30 in the system [1]-dichloromethane/methanol ratio 9/1.

$R_f$=0.62 in the system [2]-dichloromethane/methanol ratio 8/2. TLC plates-Kieselgel 60F$_{254}$ from EM-science.

IR: 2916, 2849 (alkane); 1240, 662 (methlyimidazole ring); 1740, 1172 (ester)

Compound 1 was also prepared as follows. 310 mg of 3-bromo-1,2-propanediol (2 mmol) in 3 ml of dioxane was mixed with 800 ml (10 mmol) of 1-methyl-imidazole. The reaction mixture was stirred for 16 hours at 70° C., mixed with 1,517 ml (5 mmol) of palmitoyl chloride and stirring was continued for another 24 hours at 70° C. The Title Compound 1 was purified as described above. Yield was 1326 mg (87% theoretical) of white crystal with melting point (uncorrected) of 86°±1° C. Rf=0.30 in the system [1](dichloromethane/methane mol ration 9/1). Rf=0.62 in the system [2]-dichloromethane/methane mol ratio of 8/2). TLC plates Kieselgel 60F254 from EM Science.

Compound 2

A. Structure $$CH_3(CH_2)_{14}-C(=O)-O-CH_2$$
$$CH_3(CH_2)_{14}-C(=O)-O-CH$$
$$CH_2-N(H)(CH_2)_3-O-(CH_2)_4-O-(CH_2)_3-NH_2$$

B. Synthesis 136 mg (0.2 mmol) of 1,2-dipalmitoyl-3-iodo-rac-3-deoxyglycerol was dissolved in 2 ml of dioxane and miced with 64 μl (1 mmol) of 4,9-dioxa-1,12-dodecanediamine. The reaction mixture was then stirred for 16 hours at 70° C. Dioxane was evaporated and the residue was dissolved in chloroform and mixed with an equal volume of double-distilled water. After centrifugation and separation, the water layer was discarded. This extraction with water was repeated until the water layer contained no significant mounts of amines as detected by ninhyridine reaction. The chloroform was then evaporated and the residue was re-crystallized from hot acetonitrile. Yield 134.4 mg (76% theoretical) of white crystals with:

Melting point 71°±1° C.

$R_f$=0.45 in the system [1]-dichloromethane/methanol ratio 9/1.

$R_f$=0.67 in the system [2]-dichloromethane/methanol ratio 8/2. TLC plates-Kieselgel 60$F_{254}$ from EM-science.

IR: 2919, 2851 (alkane); 1735, 1169 (ester); 1120 (ether); 3309, 840 (amine, primary); 3309, 1013 (amine, secondary)

Compound 3

A. Structure

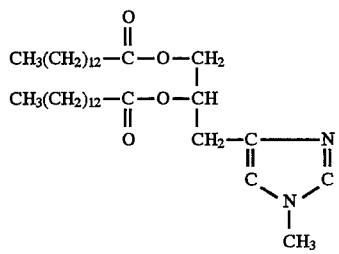

B. Synthesis 310 mg of 3-bromo-1,2-propanediol (2 mmol) in 3 ml of dioxane was mixed with 240 ml (3 mmol) of 1-methylimidazole. The reaction mixture was stirred for 16 hours at 70° C. 1.36 ml (5 mmol) of myristoyl chloride and 810 μl of pyridine (10 mmol) was added to this mixture and the reaction was continued for another 24 hours at 70° C. with stirring. Dioxane was evaporated from the reaction mixture under vacuum and the residue was re-crystallized twice from hot acetonitrile. Yield 1.0 g (87% of theor.) of white powder with:

Melting point 59°±1° C.

$R_f$=0.45 in the system [1]-dichloromethane/methanol ratio 9/1.

$R_f$=0.75 in the system [2]-dichloromethane/methanol ratio 8/2. TLC plates-Kieselgel 60$F_{254}$ from EM-science.

IR: 2920, 2855 (alkane); 1245, 663 (1-methylimidazole ring); 1727, 1168 (ester)

Compound 4

A. Structure

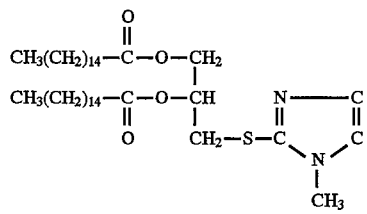

B. Synthesis 136 mg (0.2 mmol) of 1,2-dipalmitoyl-3-iodo-rac-3-deoxyglycerol was dissolved in 2 ml of dioxane and mixed with 25.1 mg (0.22 mmol) of 2-mercapto-1-methylimidazole dissolved in 2 ml of dioxane. The reaction mixture was stirred for 16 hours at 70° C. After the dioxane was evaporated, the residue was dissolved in chloroform and mixed with an equal volume of double-distilled water. After centrifugation and separation, the water layer was discarded. This extraction with water was repeated three more times. Chloroform was evaporated and the residue was dried under vacuum overnight. Yield 88 mg (66% of theor.) of white crystals with:

Melting point 53°±1° C.

$R_f$=0.20 in the system [1]-dichloromethane/methanol ratio 9/1.

$R_f$=0.60 in the system [3]-dichloromethane/methanol ratio 6/4. TLC plates-Kieselgel 60F254 from EM-science.

IR: 2919, 2851 (alkane); 1246, 663 (1-methylimidazole ring); 1741, 1163 (ester)

Compound 5

A. Structure

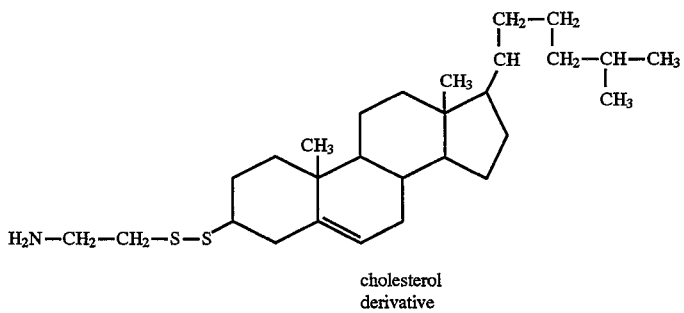

cholesterol derivative

B. Synthesis

Title Compound 5 was prepared in two steps. The first step involved synthesis of a precursor, designated Compound 5a. The structure of precursor Compound 5a is shown below.

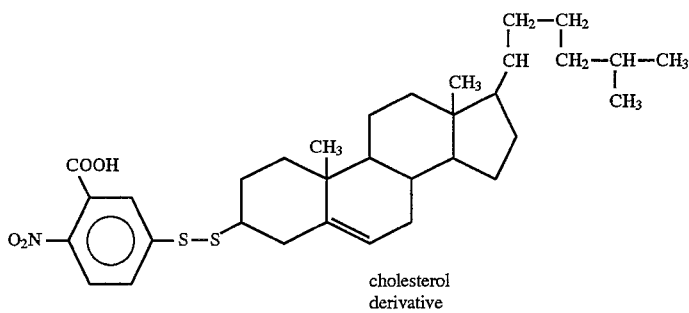

cholesterol derivative 403 mg of 3-thiocholesterol (1 mmol) solution in 10 ml of tetetrahydrofuran was mixed with 10 ml of a water solution containing 436 mg (1.1 mmol) of 5,5'-dithiobis(2-nitrobenzoic acid) in the 0.1M bicarbonate buffer, pH=7.5. After 2 hours of stirring at room temperature, a yellow precipitate of crude Compound 5a was collected as a filtrate, rinsed twice with double-distilled water, and dissolved into chloroform. The chloroform layer was extracted five times with an equal volume of double-distilled water. The water layers were combined and discarded. After the chloroform layer was evaporated, Compound 5a was dried under vacuum over night.

Yield of Compound 5a was 546 mg (91% of the theor.) of light yellow powder with:
Melting point 189°±1° C.
$R_f$=0.50 in the system [1]-dichloromethane/methanol ratio 9/1.
$R_f$=0.70 in the system [2]-dichloromethane/methanol ratio 8/2. TLC plates-Kieselgel 60F$_{254}$ from EM-science.
IR: 1465, 1372 (cholesterol); 1564 (nitro group)

60 mg (0.1 mmol) of precursor Compound 5a dissolved in 5 ml of tetrahydrofuran was mixed with 14 mg (0.12 mmol) of 2-aminoethanethiolhydrochlotide (cysteamine) dissolved in 1 ml of 0.1M bicarbonate buffer (pH=7.4). After 2 hours of stirring at room temperature, tetrahydrofuran was evaporated under vacuum. The residue was mixed with 1 ml of chloroform and the chloroform solution was extracted five times with an equal volume of double distilled water. Water layers were combined and discarded. The chloroform was evaporated and Title Compound 5 was dried under vacuum over night. Yield 45.4 mg (95% of theor.).

Melting point 170° C.±1° C.
$R_f$=0.50 in the system [1]-dichloromethane/methanol ratio 9/1.
$R_f$=1.00 in the system [2]-dichloromethane/methanol ratio 8/2. TLC plates-Kieselgel 60F$_{254}$ from EM-science.
IR: 2931, 2868 (alkane); 3404, 823 (amine primary); 1464, 1377 (cholesterol)

Compound 6

A. Structure

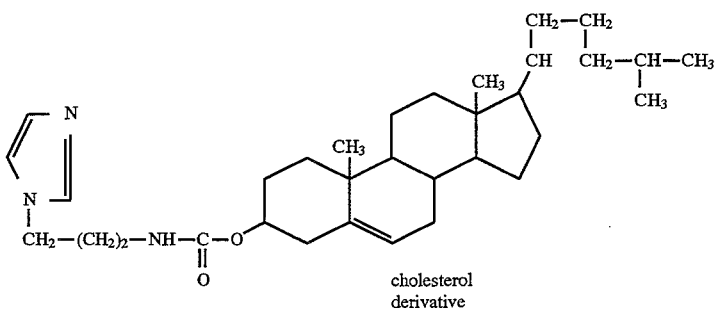

cholesterol derivative

B. Synthesis 900 mg of cholesteryl chloroformate (98%) (2 mmol) was dissolved in 10 ml of dioxane and mixed with a solution of 358 µl of 1-(3-aminopropyl)imidazole (3 mmol) in 5 ml of acetonitrile. The reaction mixture was stirred at 70° C. for 16 hours. Then, after cooling, precipitate was collected as a filtrate, rinsed with acetonitrile twice and re-crystallized from the mixture of chloroform-acetonitrile (1 volume:7 volume). Yield was 1021 mg (95% of theor).

Melting point 172°±1° C.
$R_f$=0.62 in the system [1]-dichloromethane/methanol ratio 9/1.
$R_f$=1.00 in the system [2]-dichloromethane/methanol ratio 8/2. TLC plates-Kieselgel 60F$_{254}$ from EM-Science.
IR: 2947, 2870 (alkane); 1249, 664 (1-methylimidazole ring); 3109, 1640 (amide, secondary); 1466, 1380 (cholesterol)

Compound 7

A. Structure

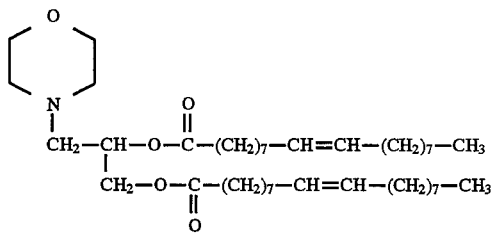

B. Synthesis 161 mg (1 mmol) of 3-morpholino-1,2-propanediol was dissolved in 3 ml of dioxane and mixed with 900 mg of oleoyl chloride (~3 mmol) and 160 ml of pyridine (~2 mmol). The reaction mixture was stirred at 70° C. for 16 hours. The dioxane was then evaporated under vacuum and the residue was dissolved in a mixture of dichloromethane/methanol (ratio 2/1 in volume). The dichlorome was slowly evaporated from the solution under vacuum in a rotary evaporator. Title Compound 7 was crystallized from methanol with yield 655 mg (95% from theor.).
Melting point 38°±1° C.
$R_f$ system[1]=0.80; $R_f$ system [2]=1.00
IR: 2931, 2868 (alkane); 1640, 960 (alkene); 1742, 1185 (ester); 1450, 1280 (N-alkylmorpholine ring)

Compound 8

A. Structure

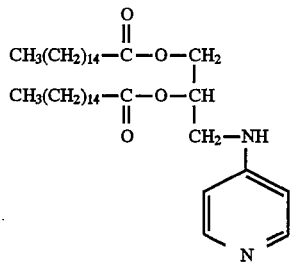

B. Synthesis 136 mg (0.2 mmol) of 1,2-dipalmitoyl-3-iodo-rac-3-deoxyglycerol was dissolved in 3 ml of dioxane and mixed with 206 mg (0.22 mmol) of 4-aminopyridine. The reaction mixture was stirred for 16 hours at 70° C. Dioxane was evaporated under vacuum and the residue was recrystallized twice from the hot acetonitrile. Yield-130 mg (84% of the theor.) of Title Compound 8 with:
Melting point 141°±1° C.
$R_f/_{system1}$=0.40; $R_f/_{system2}$=0.62
IR: 2918, 2849 (alkane); 1741, 1173 (ester); 1644, 1447 (4-aminopyridine ring)

Compound 9

A. Structure

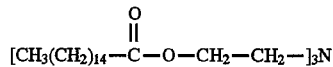

B. Synthesis 150 mg (~1 mmol) of triethanolamine was mixed with 5 ml of dioxane and 990 mg (3.6 mmol) of palmitoyl chloride. The reaction mixture was stirred for 16 hours at 70° C. Dioxane was evaporated under vacuum, the residue was dissolved in a mixture of dichloromethane/methanol (ratio 2/1) and dichloromethane was slowly evaporated from solution under vacuum in a rotary evaporator. Title Compound 9 was crystallized from methanol with yield of 787 mg (91%) of the theor.)

Melting point 40°±1° C.
$R_f/_{system1}$=0.37; $R_f/_{system2}$=0.83
IR: 2917, 2851 (alkane); 1739, 1177 (ester)

Compound 10

A. Structure

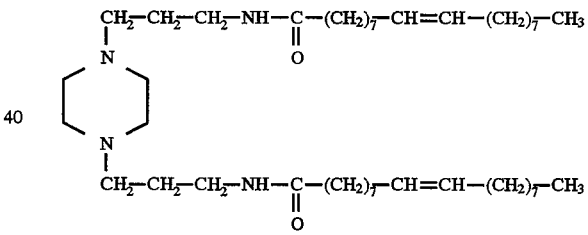

B. Synthesis 200 mg (1 mmol) of 1,4-Bis(3-aminoproryl)piperazine was dissolved in 5 ml of dioxane and mixed with 722 mg (2.2 mmol) of oleoyl chloride. The reaction mixture was stirred 16 hours at 70° C. and dioxane was evaporated under vacuum. The residue was dissolved in a mixture of dichloromethane and methanol (ratio 2/1) and dichloromethane was slowly evaporated under reduced pressure in a rotary evaporator. Title Compound 10 was crystallized with yield of 634 mg (87% of the theor.) with:

Melting point 224°±1° C.
$R_f/_{system1}$=0.30; $R_f/_{system2}$=0.80
IR: 2925, 2854 (alkane); 1635, 960 (alkene); 3076, 1641 (amide, secondary); 1466, 825 (piperazine ting)

Compound 11

A. Structure

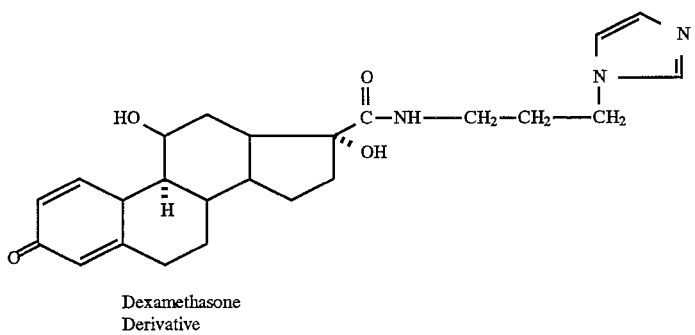

Dexamethasone Derivative

B. Synthesis 47.5 mg (0.1 mmol) of N-Hydroxysuccinimidyl-9-fluoro-16a-methyl-11β, 17 dihydroxy-3-oxo-1,4-androstadiene-17β-carboxylic acid was dissolved in 1 ml of acetonitrile and mixed with 15 mg (0.12 mmol) of 1-(3-aminopropylimidazole). N-hydroxysuccinimidyl-9-fluoro16α-methyl-11-b, 17-dihydroxy-3-oxo-1,4-androstadiene-17β-carboxylic acid can be made by methods well known to those skilled in the art. (See, for example, M. V. Govindan et al., *Eur. J. Biochem* 108, pp. 47–53, 1980). The reaction mixture was stirred for 16 hours at 50° C. After cooling the solution to 4° C., crystallized Title Compound 11 was separated by centrifugation and re-crystallized from hot acetonitrile. Yield 43 mg (85% from the theor.)
Melting point: (destruction at 230° C.)
$R_f/_{system1}$=0.20; $R_f/_{system2}$=0.80
IR: 2921, 2855 (alkane); 1242, 665 (1-methylimidazole ring); 2975, 1640 (amide, secondary); 1685, 897 (dexamethazone)

Compound 12

A. Structure

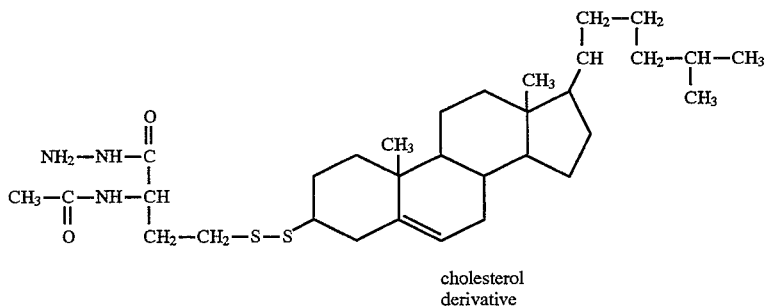

cholesterol derivative

B. Synthesis 60 mg of compound 5a (0.1 mmol) in 3 ml of tetrahydrofuran was mixed with 35 mg (0.2 mmol) of 2-acetamido-4-mercaptobutyric acid hydrazide in 2 ml of a 5% solution of sodium bicarbonate (pH 8.0) and then the reaction mixture was stirred at room temperature overnight while being protected from direct light. 2-acetamido-4-mercaptobutyric acid hydrazide may be synthesized using procedures well known to those in the art. (See, for example, K. E. Taylor et al., *Biochemiistry International* 1(4), pp. 353–358, 1980). The precipitate was filtered and rinsed with double distilled water until all traces of yellow color was removed (1max= 412 nm). The title compound 12 was collected from the filter and dried under vacuum overnight. The yield was 37 mg (64% of the theoretical yield) of slightly reddish crystals. An additional 20% yield of compound 12 can be purified from the filtrates.

Melting Point=188°C.±1° C.
$R_f$=0.20 in system [1]
$R_f$=0.90 in system [2]
IR: 2935, 2867 (alkane); 3480, 1600 (amine, primary); 3082, 1333 (amide, secondary); 1464, 1379 (cholesterol)

Compound 13

A. Structure

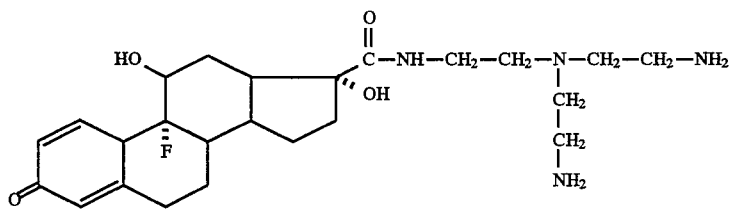

Dexamethasone Derivative

B. Synthesis 47.5 mg (0.1 mmol) of N-hydroxysuccinimidyl-9-fluoro-16α-methyl-11b, 17-dihydroxy-3-oxo-1,4-androstadiene-17β-carboxylic acid was dissolved in 1 ml of acetonitrile and mixed with 75 μl(0.5 mmol) of tris (2-aminoethyl) amine. N-hydroxysuccinimidyl-9-fluoro-16α-methyl-11b, 17-dihydroxy-3oxo-1,4-androstadiene-17β-carboxylic acid can be made by methods well known to those skilled in the art. (See, for example, M. V. Govindan et al., Eur. J. Biochem. 108, pp. 47–53, 1980). The reaction mixture was stirred at 50° C. for 16 hours, acetonitrile was evaporated and the residue was dissolved in chloroform. The chloroform layer was mixed with water (1/5 of chloroform volume). After centrifugation and separation, the water layer was extracted four more times with chloroform. The chloroform layer was evaporated under vacuum and the residue was recrystallized from acetonitrile at 4° C. Yield was 34 mg (~68% of theoretical). Title Compound 13 was a white crystal with melting point of 81° C.±1° C. $R_f$=0.00 in system [1], Rf=0.36 in system [8].

IR: 2956, 2871 (alkane); 3419, 838 (amine, secondary); 2956, 1663 (amide, secondary); 1695, 912 (dexamethazone)

Compound 14

A. Structure

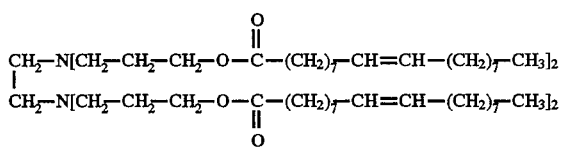

B. Synthesis 29 mg (0.1 mmol) of N,N,N'N'-tetrakis (2-hydroxypropyl)ethylene-diamine was dissolved in 2 ml of dioxane and mixed with 150 mg (~0.5 mmol) of oleoyl chloride and 65 mg of N,N-diisopropylethylamine (0.5 mmol). The reaction mixture was stirred for 16 hours at 70° C. and Title Compound 14 was purified by preparative TLC on silica gel 60F–254 TLC plates with dichloromethane as an eluent. Yield 78.3 mg (58% of the theoretical)

Melting point 38°±1° C.

$R_f/_{system4}$=0.75; $R_f/_{system1}$=1.00; $R_f/_{system2}$=1.00
IR: 2938, 2870 (alkane); 1661, 973 (alkene); 1741, 1178 (ester)

Compound 15

A. Structure

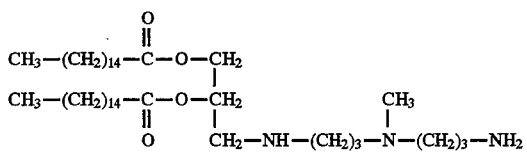

B. Synthesis 136 mg (0.2 mmol) of 1,2-dipalmitoyl-3-iodo-2rac-3-deoxyglycerol was dissolved in 3 ml dioxane and mixed with 161 ml (1 mmol) of 3,3'-diamino-N-methyldipropylamine. The reaction mixture was stirred during 16 hours at 70° C., dioxane was evaporated under vacuum and the residue dissolved in chloroform and mixed with water (⅕ of chloroform volume). After centrifugation and separation, the water layer was discarded and the extraction was repeated four more times. The chloroform layer was evaporated under vacuum and the residue was recrystallized from acetonitrile. Yield was 112 mg (68% of theoretical) of white crystals with melting point of 37° C.±1° C. Rf of 0.40 in system [1]and 0.75 in system [5].

IR: 2926, 2855 (alkane); 1740, 1180 (ester); 3430, 803 (amine, primary); 3380, 1172 (amine, secondary)

Compound 16

A. Structure

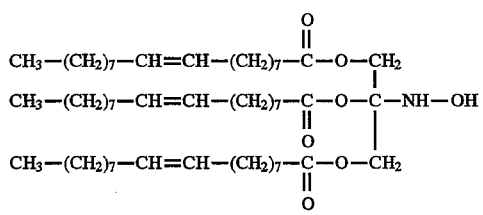

B. Synthesis

Title Compound 16 was prepared in two steps. The first step involved preparation of precursor Compound 16a, the structure of which is shown below.

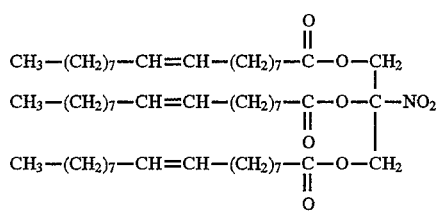

1.51 g of tris (hydroxymethyl)nitro methane (10 mmol) was mixed with 11.6 ml of oleic acid (90%) (33 mmol), 10 g of ion exchange resin Dowex 50X2-100 (H+ form) and 100 ml of dry benzene. The reaction mixture was boiled in a conical flask with a Dean-Stark receiver for 48 hours. The ion exchange resin was filtered and discarded. Benzene was evaporated from the filtrate under vacuum. The residue was dissolved in chloroform and the chloroform layer was mixed with equal volume of 3% solution of sodium bicarbonate (pH 7.5) in water. After centrifugation, the water layer and interphase were discarded, the chloroform layer was rinsed twice with water and the chloroform was evaporated under vacuum. Yield of Compound 16a was 6.8 g (72 % of theoretical). The product and had a melting point of 29° C.±1° C., with a $R_f$ of 0.65 in system [1]and 1.00 in system [2].

IR: 2925, 2854 (alkane); 1639, 967 (alkene); 1711, 1192 (ester); 1551. 1378 (nitro group)

945 mg of Compound 16a from above (1 mmol) was dissolved in 10 ml of absolute ethanol and to that solution was added 125 mg of sodium cyanoborohydride (2 mmol) slowly over 10 minutes. The reaction mixture was stirred at room temperature during two hours. Then the temperature was raised to 70° C. and the reaction mixture was stirred at 70° C. for another 16 hours. The ethanol was evaporated under vacuum and the residue was distributed between chloroform and water. After centrifugation and separation, the water layer was discarded and the extraction procedure was repeated four more times. The chloroform layer was evaporated under vacuum. Yield of Title Compound 16 was 828 mg (89% of theoretical). Melting point (light yellow liquid at room temperature). Rf of 0.60 in system [1] and 1.00 in system [2].

IR: 2927, 2855 (alkane); 1641, 967 (alkene); 1712, 1185 (ester); 1552, 723 (alkylhydroxylamine); 3330, 1042 (hydroxyl)

Compound 17

A. Structure

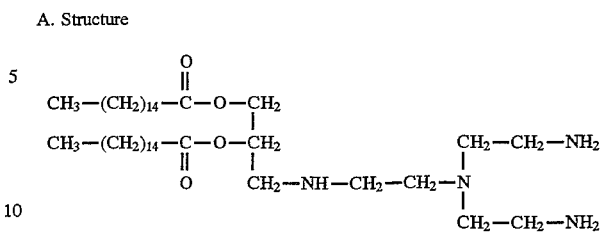

B. Synthesis 136 mg (0.2 mmol) of 1,2-dipalmitoyl-3-iodo-rac-3-deoxy-glycerol was dissolved in 2 ml of dioxane and mixed with 150 ml (1 mmol) of tris (2-aminoethyl) amine and 100 ml (~0.3 mmol) of N,N-diisopropylethylamine. The reaction mixture was stirred for 48 hours at 70° C., dioxane was evaporated under vacuum, and the residue was dissolved in chloroform and mixed with water (½ volume of chloroform). After centrifugation and separation, the water layer was discarded and the extraction was repeated four more times. The chloroform was evaporated under vacuum and the residue was re-crystallized from ethanol. Yield was 137 mg (83% of theoretical). The white powder had a melting point of 48° C.±1 ° C. $R_f$ of 0.00 in system [2]and $R_f$ of 0.70 in system [6].

IR: 2922, 2853 (alkane); 1727, 1165 (ester); 3420, 810 (amine, primary); 3322, 1113 (amine, secondary)

Compound 18

A. Structure

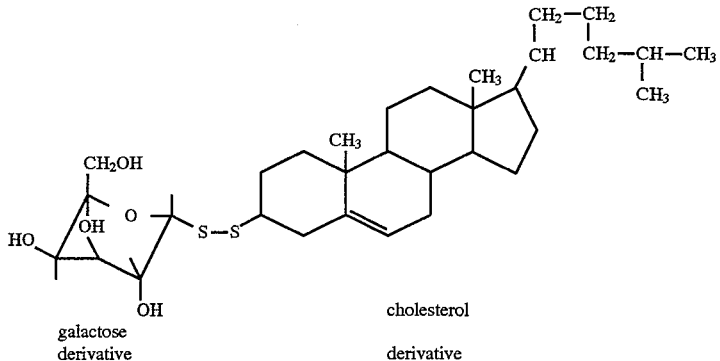

galactose derivative cholesterol derivative

B. Synthesis 60 mg of the compound 5a (0.1 mmol) in 3 ml of tetrahydrofuran was mixed with 65 mg (0.3 mmol) of the sodium salt of 1-thio-b-d-galactopyranose (Sigma Chemical) in 2 ml of a 5% solution of sodium bicarbonate (pH 8.0) and the reaction mixture was stirred at room temperature overnight wile being protected from direct light. Then, the precipitate was filtered and rinsed with water until all traces of yellow color was removed (l max=412 nm). The title compound 18 was collected from the filter and dried under a vacuum overnight. The yield was 33 mg (55% of theoretical yield) of white crystals. An additional 25% of the compound can be purified from the combined filtrates. Melting point of 198° C.±1° C., $R_f$ of 0.40 in system [1]and $R_f$ 1.00 in system [2].

IR: 2936, 2868 (alkane); 1465, 1380 (cholesterol); 1437, 1085 (thiolactopyranose)

21

Compound 19

A. Structure

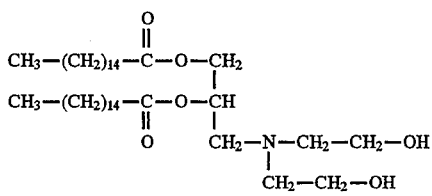

B. Synthesis 136 mg (0.2 mmol) of 1,2-dipalmitoyl-3-iodo-rac-3-deoxyglycerol was dissolved in a mixture of 2 ml of acetonitrile and 3 ml of dioxane, mixed with 100 ml (~1 mmol) of diethanolamine and stirred for 16 hours at 50° C. The dioxane and acetonitrile were evaporated under vacuum, the residue was dissolved in chloroform and the chloroform layer was mixed with water (½ volume of chloroform). After centrifugation and separation, the water layer was discarded and the extraction was repeated four more times. The chloroform layer was evaporated under vacuum and the residue was re-crystallized from acetonitrile (at 4° C.). Yield was 113 mg (86% of theoretical) of white powder with uncorrected melting point of 39°±1° C. Rf is system [1]0.62 and Rf in system [2]1.00.

IR: 2924, 2854 (alkane); 1741, 1182 (ester); 3380, 1073 (hydroxyl)

Compound 20

A. Structure

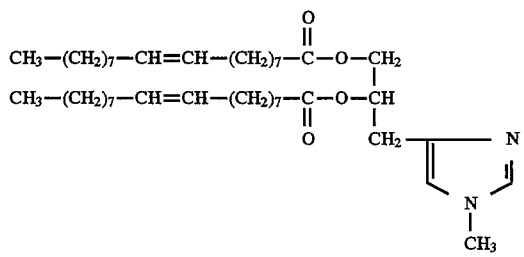

B. Synthesis 310 mg of 3-bromo-1,2-propanediol (2 mmol) in 3 ml of dioxane was mixed with ml (10 mmol) of 1-methylimidazole. The reaction mixture was stirred for 16 hours at 70° C., mixed with 1945 ml (~5 mmol) of oleoyl chloride (85%). Stirring was continued for another 24 hours at 70° C. The dioxane was evaporated under vacuum and Title Compound 20 was purified by flash chromatography (column 25×300 mm, Silica Gel G (Merck) 75–140 mm elution by step gradient of methanol in chloroform, TLC control: system 2: dichloromethane/methanol—ratio 8/2). Yield of Title Compound 20 (eluted at ratio of 95/5) was 1,118 mg (~73% of theoretical) as a light yellow liquid. Rf in system [1]0.30 and Rf in system [2]0.80.

IR: 2926, 2855 (alkane); 1641, 962 (alkene); 1241, 622 (1-methylimidazole ring); 1742, 1170 (ester)

22

Compound 21

A. Structure

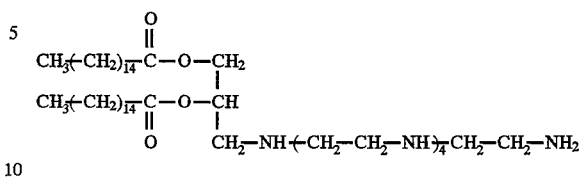

B. Synthesis 136 mg (0.2 mmol) of 1,2-dipalmitoyl-3-iodo-rac-3-deoxyglycerol was dissolved in 2 ml of dioxane and mixed with 245 ml (1 mmol) of pentaethylenehexamine. The reaction mixture was stirred for 16 hours at 70° C., the dioxane was evaporated under vacuum, the residue was dissolved in chloroform and the chloroform layer was mixed with water (⅕ volume of chloroform). After centrifugation, the water layer was separated and discarded and the extraction procedure was repeated four more times. The chloroform layer was evaporated under vacuum and the residue was crystallized from acetonitrile. Yield of Title Compound 21 was 98.5 mg (54%) as a white powder with melting point of 28° C.±1° C., Rf of 0.00 in system [2] and 0.78 in system [6].

IR: 2925, 2854 (alkane); 1740, 1190 (ester); 3577, 1600 (amine, primary); 3292, 1119 (amine, secondary)

Compound 22

A. Structure

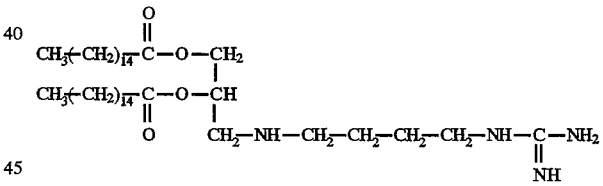

B. Synthesis 136 mg (0.2 mmol) of 1,2-dipalmitoyl-3-iodo-rac-3-deoxyglycerol was dissolved in 3 ml of dioxane and mixed with 68.5 mg (0.3 mmol) of (4-aminobutyl)guanidine sulfate (agmatine sulfate) and 52 ml (0.3 mmol) of N,N-diisopropyl-ethylaminre. Then, the reaction mixture was stirred at 70° C. overnight (16 hours) while being protected from direct light. The title compound was crystallized from the reaction mixture (at 40° C.), rinsed three times with 200 ml of cold acetonitrile and dried under vacuum overnight. The yield of compound 22 was 96 mg (70% of theoretical yield). Melting point of 85° C. +1° C., Rf of 0.40 in system [1] and Rf of 0.72 in system [2].

IR: 2954, 2918 (alkane); 1741, 1198 (ester); 3459, 1602 (amine, primary); 3382, 1118 (amine, secondary); 3056, 1310 (aminde, seondary or guanidium)

Compound 23

A. Structure

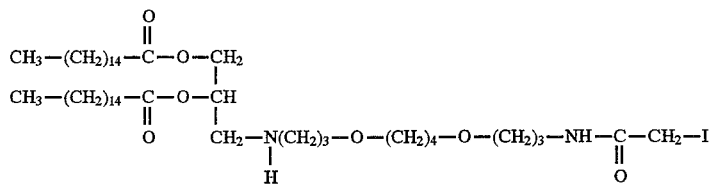

B. Synthesis

A solution of 75.6 mg of compound 2 (0.1 mmol) in 4 ml of chloroform was mixed with 20.5 mg (0.11 mmol) of iodoacetic acid, 61.8 mg (0.3 mmol) of 1,3-dicyclohexylcarbodiimide and 35 µl (0.2 mmol) of N,N-diisopropylethylamine. The reaction mixture was stirred 24 hours at room temperature while being protected from direct light and then mixed with 100 ml of water and stirred an additional two hours. The precipitate was filtered, rinsed twice with 200 ml of chloroform and discarded. The combined filtrates were mixed with 1 ml of water and the two layers were separated by centrifugation. The water layer was discarded and then the operation was repeated four more times. The chloroform layer was dried over anhydrous magnesium sulfate and evaporated under a vacuum. The title compound 23 was finally purified by preparative thin layer chromatography (system [1]) on TLC-plates-Kieselgel 60F254 from EM science. The yield was 72 mg (76% theoretical yield). Melting point of 150° C. +2° C., Rf of 0.54 in system [1] and Rf of 1.00 in system [2].

IR: 2924, 2854 (alkane); 1740, 1200 (ester); 1100 (ether); 3350, 1120 (amine, secondary); 3080, 1316 (amide, secondary)

Compound 24

A. Structure

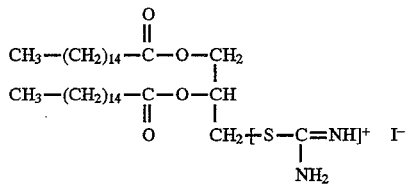

B. Synthesis 136 mg (0.2 mmol) of 1,2-dipalmitoyl-3-iodo-rac-3-deoxyglycerol was dissolved in 3 ml of dioxane and mixed with 46 mg (about 0.6 mmol) of thiourea in 1 ml of ethanol. The reaction mixture was then stirred for 16 hours at 50° C. while being protected from direct light. Then, the reaction mixture was left for 4 hours at 4° C. A white precipitate was then filtered, rinsed three times with cold acetonitrile (4° C.), three times with water (4° C.) and dried under a vacuum overnight. The yield of the title compound 24 (as white crystals) was 95 mg (63% of the theoretical yield). An additional 20 mg can be purified from the filtrate. Melting point of 85° C.+1° C., Rf of 0.00 in system [2], Rf =0.72 in system [8].

IR: 2917, 2850 (alkane); 1735, 1222 (ester); 3505, 1600 (amine, primary); 3268, 1121 (amine, secondary); 3082, 1320 (amide secondary or thiuronium)

Compound 25

A. Structure

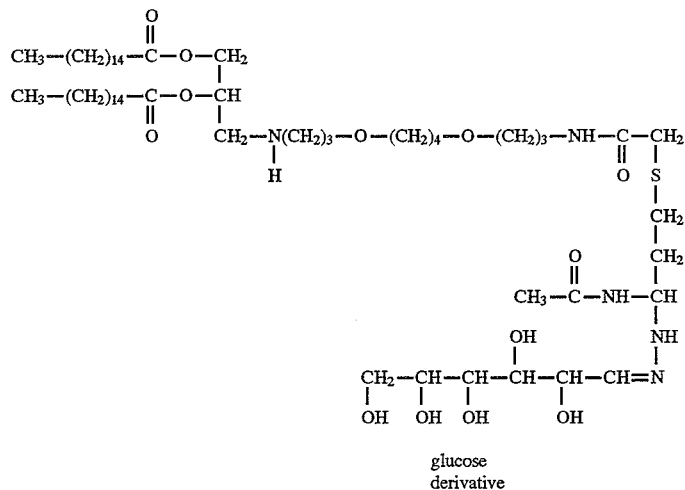

glucose derivative

B. Synthesis

A solution of 17.5 mg (0.1 mmol) of 2-acetamide-4-mercaptobutyric acid hydrazide and 54 mg (0.3 mmol) of a-d-glucose in 2 ml of water was stirred for 4 hours at room temperature. To that reaction mixture was added a solution of 47 mg (0.05 mmol) of compound 23 and 18 ml (0.1 mmol) of N,N-diisopropylethylamine in 3 ml of dioxane. Then, the reaction mixture was stirred at 37° C. for an additional 20 hours (protected from direct light), dioxane and water were evaporated under vacuum and the precipitate was distributed between chloroform (3 ml) and a 1/1 ratio mixture of water and methanol (2 ml). The top layer was separated by centrifugation. The chloroform layer was rinsed 4 more times with 2 ml (each time) of the 1/1 mixture of water and methanol mixture. Then, the chloroform was evaporated and the white precipitate obtained was dried under vacuum overnight at 40° C. The yield of the title compound 20 was 31 mg (54% of the theoretical yield). An additional amount of compound 20 can be purified from the combined water and methanol layers. Melting Point of 38° C. +1° C., $R_f$ of 0.00 in system [2] and Rf of 0.49 in system [7].

IR: 2916, 2850 (alkane); 1738, 1223 (ester); 1102 (ether); 3360, 1119 (amine, secondary); 3086, 1324 (amide, secondary); 3332, 1080 (hydroxyl)

EXAMPLE 2

3T3 Cells Transfected with DNA-Compound 20 Ethanol Solutions

Conventional liposomes were prepared by mixing chloroform solutions of the different lipids in Fisherbrand* Microcentrifuge Tubes with Screw Caps at 1.5 ml and removing the chloroform by SpeedVac SVC100 (Savant) to produce the dried lipid films. Tubes were placed under vacuum overnight to remove solvent traces. The amount of cationic lipids in all cases were 1.34 umol/ml with different amounts of other lipids as specified. One ml of sterile 10 mM HEPES buffer pH 7.8 was added, and the tubes were sealed and vortexed for 1 min. at room temperature and then sonicated in Bath Sonicator Branson 2200 to obtain a clear emulsion.

Cell Culture—Mouse 3T3 fibroblasts were maintained in Dulbeco's Modified MEM media supplemented with 10% fetal calf serum. All cultures were maintained in a humidified atmosphere of 5% $CO_2$ in air at 37° C. The cells were seeded in a 6-well plate (35 mm culture dishes) or a 12 well-plate (25 mm culture dishes) 24 h before the transfection at 70% confluence. Before transfection, the cells was washed once with Opti-MEM. In case of the 35 mm culture dishes, four ug of plasmid DNA (containing the luciferase or β-galactosidase reporter genes described below) in 0.75 ml of OptiMEM was mixed with various amounts of liposomes in 0.75 ml of Opti-MEM. In case of the 25 mm culture dishes, one or two mg DNA in 400 ml of Opti-MEM was mixed with 400 ml of liposomes in 400 ml of Opti-MEM. The mixtures were incubated for 30 min at room temperature prior to being added to the cells in the culture dish. The cells were incubated at 37° C. in 5% $CO_2$/95% air. After four hours, the transfection mixture was removed and replaced with 0.75 ml and 1.5 ml of DMEM +10% FCS for 25 mm and 35 mm plates, respectively. The cultures were incubated for 24 hours until they were harvested for analysis of their reporter gene expression.

Transfections requiring only plasmid DNA and Lipofectin™ (GIBCO BRL), lipofectAMINE™ (3:1 (w:w) ratio of DOSPA which is 2,3-dioleyloxy-N-[20({2,5-bis[(3-aminopropyl)amino]-1-oxypentyl }amino)ethyl]-N,N-dimethyl-2,3-bis(9-octadecenyloxy)-1-propanaminium trifluoroacetate and DOPE) (GIBCO BRL),TransfectACE™ (1:2.5 (w:w) ratio of DDAB which is dimethyl dioctadecylammonium bromide and DOPE) (GIBCO BRL) or DOTAP (N-[1-(2,3-dioleoyloxy) propyl]-N,N,N-trimethyl-ammoniummethylsulfate) were also prepared according to the manufacturers' recommendations.

Use of Reporter Genes

The firefly luciferase and E. coli β-galactosidase reporter genes were used to determine the efficiency of DNA transfer quantitatively. The previously described, plasmid DNA pBS.RSVLux was used to express the firefly luciferase reporter gene from the Rous Sarcoma Virus (RSV) LTR promoter. The plasmid also contains the SV40 intron and poly A addition signals for proper and efficient mRNA processing. The β-galactosidase expression plasmid, pBS.CMVLacZ was derived from pCMVb-gal by placing the CMV promoter, β-galactosidase coding sequence and the SV40 intron/poly A sequences within pBluescript KS- (Stratagene). All plasmids were purified by alkaline lysis and then two cesium chloride gradients as previously described.

Reporter Gene Assays

For determination of luciferase activity, cells were lysed by the addition of 100 μl for 25 mm plates and 200 μl for 35 mm plates of lysis buffer (0.1% Triton X-100, 0.1M K-phosphate, 1 mM DTT, pH 7.8). 20 μl of the cellular extract were analyzed for luciferase activity and expressed as Light Units/20 μl.

For determination of β-galactosidase activity, the cells in 12-well plate were lysed with 100 ml of 0.1% Triton X-100, 250 mM Tris, pH 8.0. 50 ml of the cell suspension was placed in wells of a 96-well plate and 150 ml of ortho-nitrophenol galactopyranoside (2 mg/ml) in 60 mM sodium phosphate pH 8.0, 1 mM $MgSO_4$, 10 mM KCl, 50 mM β-mercaptoethanol was added. After 4 hours of incubation at 37° C., optical density at 405 nm in every wall was determined in a microtiter plate reader (Dynatech MR250).

The amount of soluble protein in extracts was determined by the BCA Protein Assay Reagent (Pierce, Co., Rockford, Ill.) assay in 20 ml of extract. No DTT was used in the cellular lysis buffer when protein assays were done. The cells were also washed with normal saline to remove residual serum. This determination of protein concentration enabled the specific activity of reporter protein to be determined. The measurement of cellular protein was also used as indication of cellular survival following exposure to the liposome/DNA complexes and therefore indicated the toxicity of the liposome/DNA complexes.

For preparation of the DNA-Compound 20 ethanol solution the pBS.RSVLux DNA in concentration of 4 mg/ml (milligram/milliliter) was mixed with equal volume of 50% ethanol and then diluted ten-fold more by 96% ethanol to a final concentration of 0.2 mg/ml DNA. Solutions of Compound 20 in 96% ethanol were prepared with the following four concentrations of Compound 20: 0.4, 0.8, 1.2, and 1.6 mg/ml. The equal volumes of DNA and lipid solution were mixed. As a result four DNA-lipid solutions in 93% ethanol were prepared with concentration of DNA of 100 ug/ml and the ration of DNA/lipid (w/w) of 1:2, 1:4, 1:6 an 1:8. Different volumes of the DNA-ethanol solutions were diluted in 0.5 ml of OptiMEM (Gibco/BRL, Life Technologies) and immediately added to 3T3 cells (mouse fibroblasts) in 1 ml of OptiMEM on 35 mm 6-well tissue culture plates. The cells were exposed to the DNA-lipid mixture for 4 hours while being incubated at 37° C. Afterwards the media were replaced with D-MEM (Gibco/BRL, Life Technologies) plus 10% fetal calf serum (Hyclone). The cells were then incubated for an additional 36 hours before they were harvested for luciferase assays. The transfection with the conventional liposome preparation of Lipofectin (Gibco/BRL, Life Technologies) was performed with 2 μg of pBS.RSVLux and is shown for control purposes.

| Volume (10 μl) | Lipofectin | DNA/ Compound 20 (1:2) | DNA/ Compound 20 (1:4) | DNA/ Compound 20 (1:6) | DNA/ Compound 20 (1:8) |
|---|---|---|---|---|---|
| 10 | 308,936 | | | | |
| 20 | | 1,581 | 148,007 | 101,844 | 167,443 |
| 40 | | 1,542 | 367,273 | 964,289 | 1,370,259 |
| 70 | | 762 | 287,394 | 430,090 | 409,734 |
| 100 | | 46,063 | 32,656 | 395,528 | 226,072 |

These results demonstrate the DNA-Compound 20 ethanol solutions containing novel complexes of DNA and amphipathic compounds can mediate the efficient transfection of mammalian cells in culture.

EXAMPLE 3

Binding of Fluorescently-Labeled Oligonucleotides to 3T3 cells

A 25-mer oligo Adenylic acid (A) with an amino group on the 3'-end was obtained from (Integrated Genetics). Fluorescein isothiocyanate (FITC) (Molecular Probes Corp.) was mixed with the oligo A in 10 mM-Na-Phosphate buffer (pH 7.5) and incubated five hours at room temperature. The non-attached FITC was removed by gel-filtration on Sephadex-G 25. The FITC-labelled oligo-A were prepared with conventional liposomes or according to the method described in Example 2.

For preparation of the Liposome-oligonucleotide complexes, 6 μl (2.4 μg) of FITC-oligo-A were mixed with 10 μl of Lipofectin or DPIm/DOPE (1 mg/ml of each Compound #) in 200 μl of Opti-MEM. The liposome complexes were incubated at room temperature for 20 min. before being added to the tissue culture plates.

The Compound 20-oligonucleotide complexes in ethanol were prepared as follows. 6 μl (2.4 μg) of FITC-oligo-A and 6 μl of 70% ethanol were mixed. To this mixture, 20 μl of 70% ethanol solution of Compound 20 (1 mg/ml) was added. The mixtures were added to 3T3 cells in 1.5 ml of Opti-MEM in 35-mm plates. After 3 hours of incubation on ice or at 37° C., the cells were washed four times with phosphate buffered saline (PBS) and extracted with 0.8 ml of 0.1% Triton-X-100 in PBS. The fluorescence of the extracts were determined using a Fluorescent Spectrophotometer (Hitachi F-3010). Fluorescence in cell extracts are shown below as the mean±range of duplicates.

| Preparation of FITC-Oligo-A | 4° C. | 37° C. |
|---|---|---|
| Alone | 0.40 ± 0.33 | 0.46 ± 0.13 |
| Lipofectin | 6.27 ± 0.50 | 2.10 ± 0.14 |
| DPIm/DOPE | 0.14 ± 0.01 | 0.39 ± 0.17 |

-continued

| Preparation of FITC-Oligo-A | 4° C. | 37° C. |
|---|---|---|
| Liposomes Compound 20 Micelles | 39.19 ± 0.46 | 41.11 ± 0.16 |

These results demonstrate that an oligonucleotide was delivered to a mammalian cell with the most efficiency when it was complexed with Compound 20 micelles. Liposome form of almost identical compound 1 was unable to deliver oligonucleotides at described conditions.

EXAMPLE 4

The Effect of Anti-Sense Oligonucleotides on Luciferase Expression in 3T3 Cells

A Lux anti-sense (GGCGTTCTTCCATTTTACC) was prepared to be complementary to the luciferase sense sequence around its initial codon. For control purposes, the Lux sense (GGTAAAATGGAAGACGCC) oligonucleotide was also prepared. The oligonucleotides were obtained from Integrated DNA Technology Corp.

The 3T3 cells were transfected with pBS.RSVLux using Lipofectin. At 24 hours after transfection, the cells were treated with the 10 μg of oligonucleotides alone or complexes with conventional Compound 20 liposomes or Compound 20 micelles. 80 μl and 40 μl of Compound 20 liposomes (1 mg/ml) were used in experiments #1 and #2, respectively. In experiment #1, the Compound 20/oligonucleotide ethanol solutions were prepared by mixing 80 μl of 1 mg/ml of Compound 20 in 70% ethanol and 60 μl of 50% ethanol without or with 10 μg of the oligonucleotides. In experiment #2, the Compound 20/oligonucleotide ethanol solutions were prepared by mixing 40 μl of 1 mg/ml of Compound 20 in 70% ethanol and 20 μ of 35% ethanol without or with 10 μg of the oligonucleotides. The cells were assayed for luciferase 2 hours after exposure to the oligonucleotide formulations at 37° C. in an $CO_2$ incubator.

The percentage of luciferase expression from the pBS.RSVLux-transfected cells subsequently exposed to the preparations without oligonucleotides as compared to the luciferase expression from the pBS.RSVLux-transfected cells subsequently exposed to the preparations with oligonucleotides is shown below.

| Oligonucleotide Type | Experiment # | Type of Preparation | | |
|---|---|---|---|---|
| | | No Liposome | DPIm Liposome | Compound 20 Micelle |
| anti-sense | #1 | 71.6% | 91.6% | 37.9% |
| | #2 | 99.7% | 73.5% | 46.0% |
| sense | #1 | 97.9% | 96.8% | 84.9% |
| | #2 | 107.8% | 90.8% | 121.1% |

These results demonstrate that anti-sense oligonucleotides prepared in ethanol with Compound 20 quenched luciferase expression much more than anti-sense oligonucleotides without liposomes (naked oligonucleotides) or complexed with conventional liposomes and any of the preparations of the control sense oligonucleotides. Given that the half life of luciferase protein is approximately two to three hours, it is estimated that the anti-sense oligonucleotide-Compound 20 ethanol mixture inhibited approximately 100% of the luciferase mRNA. Lipofectin complexes with oligonucleotides did not result in any inhibition even though it delivered relatively large amounts of oligonucleotides to the cells. One possible reason is that the dissociation rate for lipofectin complexes is very low. The imidazole derivatives within liposome preparations do not bind oligonucleotides strongly and this provides further evidence for an unique property of the micelle complex.

EXAMPLE 5

Interactions of DNA/Compound 20 Micelles with a DNA Intercalator (TOTO)

The DNA Intercalator, TOTO, was used as a probe to determine whether the DNA within the Compound 20 micelles was accessible or not. The fluorescence of the TOTO compound increases substantially when it binds to DNA. Preparation of the DNA-Compound 20 micelles were as above. The pBS.RSVLux DNA in concentration of 4 mg/ml (milligram/milliliter) was mixed with equal volume of 50% ethanol and then diluted ten-fold more by 96% ethanol to a final concentration of 0.2 mg/ml DNA. Solutions of Compound 20 in 96% ethanol were prepared with he following four different concentrations of Compound 20: 0.4, 0.8, 1.2, and 1.6 mg/ml. The equal volumes of DNA and lipid solution were mixed. The TOTO (Molecular Probes) solution was 5 µM. 10 µl (1 µl of DNA) of each solution was dissolved in 1 ml of water and 20 µl of the TOTO solution was added. The fluorescence (excitation=509 nm; emission=533 nm) was determined immediately and after 40 min. No time dependence of the fluorescence was noted. The 50 µl of 1% Triton-X-100 was added to disrupt the micelles and the fluorescence was re-measured. The fluorescence was normalized to the amount of fluorescence when no lipid was present.

| Lipid/DNA Ratio (w/w) | Percent Fluorescence | | % Accessibilty |
|---|---|---|---|
| | Without Triton-X100 | With Triton-X100 | |
| 0 | 100 | 100 | 100 |
| 0.25 | 91 | 96 | 95 |
| 0.5 | 85 | 104 | 82 |
| 1 | 51 | 102 | 50 |
| 2 | 9 | 101 | 9 |
| 4 | 1 | 74 | 1 |
| 8 | 1 | 62 | 2 |

These results demonstrate that DNA within the micelles is not accessible to interaction with compound TOTO. This indicates that the DNA is encapsulated within the Micelles.

Examples have been included to illustrate preferred modes of the invention. Certain aspects of the Examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the Examples are intended to be exemplary only and that numerous changes, modifications and alterations can be employed without departing from the spirit and scope of the invention.

---

What is claimed is:

1. A composition comprising a population of micelles wherein each micelle comprises at least one amphipathic compound layer that surrounds a non-aqueous core that contains a polyion, wherein the amphipathic compound has the structure:

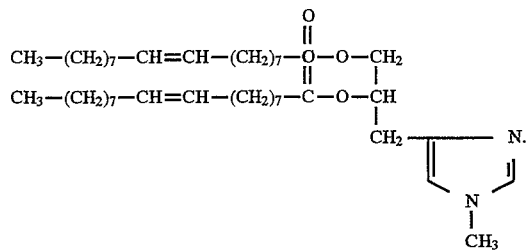

2. A process of preparing a population of mixed micelles comprising mixing an amphipathic compound with a polyion in an aqueous solution containing at least fifty volumes percent of a water-soluble organic solvent to form the micelles.

3. The process according to claim 2 wherein the water-soluble organic solvent is ethanol, isopropanol, methanol, or acetonitrile.

4. A process of preparing a population of mixed micelles comprising mixing an amphipathic compound with a polyion in an aqueous solution containing at least fifty volumes percent of a water-soluble organic solvent to form the micelles; and mixing the micelles with a second amphipathic compound to form an admixture and decreasing the concentration of the water-soluble organic solvent in the admixture.

5. A process of preparing a population of mixed micelles comprising mixing an amphipathic compound with a polyion in an aqueous solution containing at least fifty volumes percent of a water-soluble organic solvent to form the micelles, wherein the amphipathic compound has the structure:

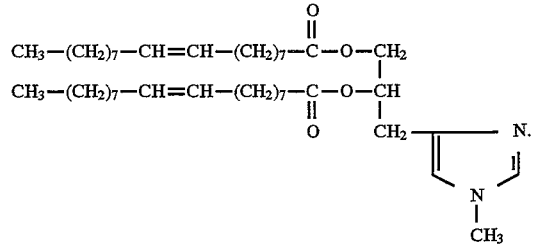

* * * * *